United States Patent [19]
Camaggi et al.

[11] Patent Number: 6,084,065
[45] Date of Patent: Jul. 4, 2000

[54] OLIGOPEPTIDES WITH FUNGICIDAL ACTIVITY

[75] Inventors: Giovanni Camaggi, Novara; Lucio Filippini, San Donato Milanese; Marilena Gusmeroli, Monza; Carlo Garavaglia, Cuggiono; Ernesto Signorini, Malnate, all of Italy

[73] Assignee: Isagro Spa, Milan, Italy

[21] Appl. No.: 08/317,767

[22] Filed: Oct. 4, 1994

[30] Foreign Application Priority Data

Oct. 5, 1993 [IT] Italy .................................. MI93A2113

[51] Int. Cl.$^7$ .............................. A61K 38/06; C07K 5/00; C07K 7/00; C07K 16/00
[52] U.S. Cl. .............................. 530/331; 514/18; 514/19; 514/368; 560/37; 560/40; 560/41; 564/152; 564/153; 564/154; 564/155
[58] Field of Search ................................ 514/18, 368, 19; 530/331; 560/37, 40, 41; 564/152, 153, 154, 155

[56] References Cited

U.S. PATENT DOCUMENTS

| | | |
|---|---|---|
| 4,425,357 | 1/1984 | Bosone et al. . |
| 5,013,723 | 5/1991 | Sisto . |
| 5,200,506 | 4/1993 | Sisto . |
| 5,378,707 | 1/1995 | Camaggi et al. . |
| 5,384,325 | 1/1995 | Camaggi et al. . |
| 5,464,836 | 11/1995 | Camaggi et al. . |
| 5,556,829 | 9/1996 | Camaggi et al. . |
| 5,652,336 | 7/1997 | Fife . |
| 5,691,368 | 11/1997 | Peet . |
| 5,716,974 | 2/1998 | Camaggi et al. ........................ 514/368 |

FOREIGN PATENT DOCUMENTS

| | | |
|---|---|---|
| 363284 | 4/1990 | European Pat. Off. . |
| 62-084099 | 4/1987 | Japan . |
| 9208698 | 5/1992 | WIPO . |

OTHER PUBLICATIONS

Frey et al Peptide: Struct. Funct. Proc. Am. Pept. Symp. 8$^{th}$ pp. 763–771, 1983.
Blumberg et al Eur. J. Biochem 136(1):151–154, 1983.
Ando et al, Fukuoka Daigaku Rigaku Shuho 10/1:7/12, 1980.
Rich et al, J.Med. Chem. 35/21: 3803–3812, 1992.
Kovalenko et al Fiziol. Akt. Veschchestva 13:81–84, 1981.
Bland et al, Pestic Sci, 39:331–340, 1993.
Cavelier et al, Tetrahedron 52/17: 6173–6186, 1996.
Kopple, K. in "Peptides and Amino Acids", W. A. Benjamin, New York (1966). See Ch. 3 pp. 33–41.
Catalog S13, p. 334, achem Feinchemikalien Ag, Switzerland, 1993.
Chemical Abstracts, vol. 119, Jul. 5, 1993 No. 1, Abstract, No. 9137h.
Chemical Abstracts, vol. 109, Nov. 7, 1988 No. 1, Abstract No. 165707t.
Anderson, P. et al. "Preparation of tetrahydroisoquinolinyl-carbonylpeptides as inhibitors of HIV protease and renin." European Patent Application No. EP 401676 published Dec. 12, 1990. See abstract.
Cleij, M. et al. (1993) Mechanism of enantioselective ester cleavage by histidine containing dipeptides at a micellar interface. *J. Org. Chem.* 56, 3883–91. See abstract.
El–Naggar, A. et al. (1990) Synthesis of some . . . and their antimicrobial activity. *J. Serb. Chem. Soc.* 55, 441–448. See abstract.
Ibrahim, T. et al. (1993) Synthesis of new biologically active furan derivatives. *Indiana J. Heterocycl. Chem.* 3, 127–131. See abstract.
Myers, P. et al. "Preparation of peptide cyclic imide derivatives as tissue degradation inhibitors." European Patent Application No. EP 520573 published Dec. 30, 1992. See abstract.

*Primary Examiner*—Nita Minnifield
*Attorney, Agent, or Firm*—Kramer Levin Naftalis & Frankel LLP; A. David Joran

[57] ABSTRACT

The present invention relates to oligopeptidic compounds having the general formula (I):

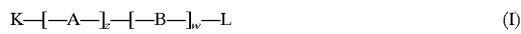

$$K-[-A-]_z-[-B-]_w-L \qquad (I)$$

The compounds having general formula (I) are antifungals for agricultural purposes.

20 Claims, No Drawings

OLIGOPEPTIDES WITH FUNGICIDAL ACTIVITY

The present invention relates to oligopeptidic compounds.

More particularly, the present invention relates to oligopeptidic compounds having high antifungal activity, to a process for preparing them and to their use in agricultural field as fungicides.

Therefore, the subject-matter of the present invention are oligopeptidic compounds having the general formula (I):

wherein:

z and w, which may be the same or different from each other, are 1 or 2;

A represents an aminoacidic portion having the general formula (II):

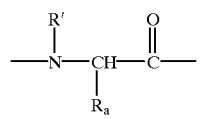

wherein:

$R_a$ represents a linear or branched $C_3$–$C_4$ alkyl radical; or a $C_3$–$C_4$ cycloalkyl radical;

R' represents a hydrogen atom; a $C_1$–$C_3$ alkyl radical; or, together with $R_a$, represents a $C_3$–$C_5$ alkylene chain;

B represents an aminoacidic portion having the general formula (III):

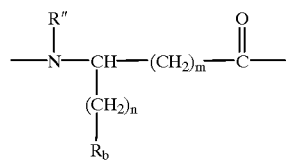

wherein:

$R_b$ represents a phenyl radical, an aromatic heterocyclic radical or a naphthyl radical, with said phenyl, heterocyclic and naphthyl radicals being also optionally substituted;

an aromatic benzofused five-membered heterocyclic radical containing from 1 to 2 heteroatoms, which may be the same or different from each other, selected from nitrogen, oxygen and sulfur, with said aromatic benzofused five-membered heterocyclic radical being also optionally substituted;

m and n, which may be the same or different from each other, are 0 or 1;

R" represents a hydrogen atom or a $C_1$–$C_3$ alkyl radical;

L represents a moiety having the general formula (IV):

wherein:

E represents an either linear or branched $C_1$–$C_8$ alkylene or haloalkylene chain; an omega oxa-$C_2$–$C_8$-alkyl chain; or a direct linkage;

$R^1$ represents a hydrogen atom; a $C_3$–$C_6$ cycloalkyl radical; a phenyl radical or an aromatic heterocyclic radical, with said phenyl and heterocyclic radicals being also optionally substituted;

$R^2$ represents a hydrogen atom; a linear or branched $C_2$–$C_6$ carboxyalkyl radical; a linear, branched or cyclic $C_2$–$C_6$ carbamoyl radical; a cyano radical; or an halogen atom selected from fluorine, chlorine and bromine;

X represents an —O— moiety; a —N($R^3$)— moiety or a —N($R^4$)—O— moiety; wherein:
  $R^3$ represents a hydrogen atom; a $C_1$–$C_3$ alkyl or alkoxy radical; or, together with $R_1$, represents a direct linkage or a $C_2$–$C_4$ alkylene chain;
  $R^4$ represents a hydrogen atom; a $C_1$–$C_3$ alkyl radical; or, together with $R_1$, represents a direct linkage, with the proviso that X represents an —O— moiety, and E represents a direct linkage, only one of $R^1$ and $R^2$ is present;

K represents a hydrogen atom; an either linear or branched $C_1$–$C_4$ alkyl radical; or a protective group having the general formula (V):

wherein:

Y represents an oxygen atom; or a direct linkage;

M represents an either linear, branched or cyclic $C_1$–$C_8$ alkylene or haloalkylene chain; or a direct linkage;

$R^5$ represents a hydrogen atom; an optionally substituted phenyl radical; an optionally substituted phenoxy radical; an optionally substituted thiazolic radical; a linear, branched or cyclic $C_2$–$C_6$ carbamoyl radical; a linear, branched or cyclic $C_1$–$C_6$ carbalkoxy radical; or a cyano radical;

$R^6$ represents a hydrogen atom; a $C_1$–$C_3$ alkoxy or haloalkoxy radical; an acetate radical; an acetamidic radical; or an halogen atom selected from fluorine, chlorine and bromine, with the proviso that when Y represents and oxygen atom, and m represents a direct linkage, only one of $R^5$ and $R^6$ is present.

The structure having the general formula (I) contains two or more chiral centres. Purpose of the present invention is to take into consideration both isomerically pure compounds having general formula (I), as well as mixtures thereof.

The compounds having general formula (I) are antifungal agents for agricultural purposes.

By "aromatic heterocyclic radical", an aromatic 5-membered or 6-membered heterocyclic radical is understood, which contains from one to three heteroatoms, which may be the same or different from each other, and are selected from nitrogen, oxygen and sulfur.

When a phenyl radical, an aromatic heterocyclic radical, a naphthyl radical or an aromatic benzofused five-membered heterocyclic radical containing from 1 to 2 heteroatoms, which may be the same or different from each other, is disclosed as being "optionally substituted", it should be understood that said radical may be substituted with one or more halogen atoms, which may be the same or different from each other, and are selected from fluorine, chlorine, bromine and iodine, or with one or more groups, which may be the same or different from each other, and are selected from either linear or branched $C_1$–$C_5$ alkyl or haloalkyl radicals, either linear or branched $C_1$–$C_5$ alkoxy or haloalkoxy radicals; $C_3$–$C_6$ cycloalkyl or cycloalkoxy radicals; $C_2$–$C_5$ carbalkoxy radicals; cyano radicals; methylene dioxyl radicals having the general formula (VI):

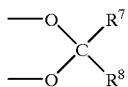

(VI)

wherein:

$R^7$ and $R^8$, which may be the same or different from each other, represent a hydrogen atom, a fluorine atom; a $C_1$–$C_3$ alkyl or haloalkyl radical.

When a phenoxy radical or a thiazolic radical is disclosed as being optionally substituted, it should be understood that said radical may be substituted with one or more halogen atoms, which may be the same or different from each other, selected from fluorine, chlorine, bromine and iodine, or with a methyl or trifluoromethyl radical.

Examples for $R_a$ radicals, when $R_a$ represents an alkyl radical, are: isopropyl, isobutyl, sec.-butyl, tert.-butyl, and so forth.

Examples for aminoacidic radicals A, when $R_a$ represents an alkyl radical, are (in brackets, the short form is reported which is derived from the international symbology used for peptides): L-Valine (-L[Val]-), DL-Valine (-DL[Val]-), D-Valine (-D[Val]-), Leucine (-[Leu]-), Isoleucine (-[Ile]-), allo-Isoleucine (-a[Ile]-), tert.-Leucine (-[Tle]-), and so forth.

Examples of $R_a$ radicals, when $R_a$ represents a cycloalkyl radical, are: cyclopropyl, methylcyclopropyl, dimethylcyclopropyl, and so forth.

Examples of aminoacidic radicals A, when $R_a$ represents a cycloalkyl radical, are: cycloprolylglycine, cyclobutylglycine, and so forth.

Examples of aminoacidic radicals A, when R', together with $R_a$, represents a $C_3$–$C_5$ alkylene chain, are: proline (-[Pro]-), 3-methylproline (-[Pro](3-Me)-), 3,3-dimethylproline (-[Pro](3,3-Me$_2$)-), and so forth.

Examples of aromatic five-membered or hexa-membered heterocyclic radicals containing from one to three heteroatoms, which may be the same or different from each other, and are selected from nitrogen, oxygen and sulfur, are: pyridine, pyrimidine, pyrrole, imidazole, triazole, thiazole, oxazole, isooxazole, and so forth.

Examples of aminoacidic residues B, when $R_b$ represents an optionally substituted phenyl radical and n is 0, are: D-Phenylglycine (-D[Phg]-), DL-$^P$henylglycine (-DL[Phg]-), DL-p-Cl-Phenylglycine (-DL[Phg](4-Cl)-), and so forth.

Examples of aminoacidic radicals B, when $R_b$ represents an optionally substituted phenyl radical and n is equal to 1, are: D-Phenylalanine (-D[Phe]-), DL-Phenylalanine (-DL[Phe]-), D-Tyrosine (-D[Tyr]-), DL-Tyrosine (-DL[Tyr]-), DL-Tyrosine-methylether (-DL[Tyr](Me)-), DL-3-methoxy-Tyrosine-methylether (-DL[Tyr](Me)(3MeO)-), DL-β-Phenylalanine (-DL-β[Phe]-), β-Tyrosine-O-methylether (-β[Tyr](Me)-), and so forth.

Examples of aminoacidic residues B, when $R_b$ represents an optionally substituted aromatic heterocyclic radical and n is equal to 0, are: (1-methylpyrrol-2-yl)glycine, imidazol-2-yl-glycine, thiazolyl-2-glycine, (4-phenyl-3-methylthiazol-2-yl)-glycine, (5-trifluoromethylpyrid-2-yl)glycine, pyrimidin-2-yl-glycine, and so forth.

Examples of aminoacidic residues B, when $R_b$ represents an optionally substituted aromatic heterocyclic radical and n is equal to 1, are: 3-(1-methylpyrrol-2-yl)alanine, 3-(imidazol-2-yl)alanine, 3-(thiazol-2-yl)alanine, 3-(5-trifluoromethylpyrid-2-yl)alanine, 3-pyrimidin-2-yl-alanine, 3-[(3-methoxy-4-methyl)isooxazol-5-yl]alanine, and so forth.

Examples of L, when X represents an oxygen atom, are: methoxy, ethoxy, isopropoxy, tert.-butoxy, benzyloxy, and so forth.

Examples of L, when X represents a —N($R^3$)— moiety, are: methylamino, isopropylamino, butylamino, octylamino, N,N-dimethylamino, piperidyl, morphol-4-yl, benzylamino, 4-chlorobenzylamino, 2,4-dichlorobenzylamino, α-methyl-4-chlorobenzylamino, α-methyl-4-bromobenzylamino, α-methyl-4-methoxy-benzylamino, α-methyl-4-trifluoromethylbenzylamino, thiazol-2-ylamino, imidaz-2-ylamino, α-cyanobenzylamino, α-cyanoisopropylamino, α-carbomethoxyethylamino, α-carboisopropoxy-ethylamino, α-carbomethoxyisobutylamino, 2-carboisopropoxypyrrolid-1-yl, α-(N-methylcarbamoyl)ethylamino, α-carbamoylethylamino,2-(N,N-dimethylcarbamoylpyrrolid-1-yl),2-(N,N-dimethylcarbamoylpiperid-1-yl), and so forth.

Examples of L, when X represents an —N($R^4$)—O— moiety, are: methoxyamino, benzyloxyamino, N-methyl-N-benzyloxyamino, and so forth.

Examples of K, when Y represents an oxygen atom, are: carbomethoxy, carboisopropoxy, carboisobutoxy, carbo-tert.-butoxy, carbobenzyloxy, carbophenoxy, and so forth.

Examples of K, when Y represents a direct bond, are: acetyl, isobutanoyl, benzoyl, cyclopropanoyl, 2-methoxy-propanoyl, 2-acetamidopropanoyl, 2-carbomethoxyacetyl, and so forth.

Compounds having the general formula (I) not illustrated in the examples, but equally interesting for their fungicidal activity, are (the compounds reported hereinunder, are represented in accordance to the international symbology used for peptides):

Me$_2$—CH—O—CO-[Val]-[Phg]-O—Me;
Me$_2$—CH—O—CO-[Val]-[Phg]-O—CH—Me$_2$;
Me$_2$—CH—O—CO-[Val]-[Phe]-O—CH—Me$_2$;
Me$_2$—CH—O—CO-[Val]-[Phg]-O—CH(Me)—CO—NH—iPr;
Me$_2$—CH—O—CO-[Val]-[Phg]-O—CH(Me)—CO-piperidyl;
Me$_2$—CH—O—CO-[Val]-[Phg]-N(Me)—Me;
Me$_2$—CH—O—CO-[Val]-[Phg]-piperidyl;
Me$_2$—CH—O—CO-[Val]-[Phg]-NH—CH(Me)-pCl-phenyl;
H-[Val]-[Phg]-NH—CH(Me)-pCl-phenyl;
Me$_3$—C—O—CO-[Val]-[Phg]-NH—CH(Me)-pCl-phenyl;
Me$_2$—CH—CH$_2$—O—CO-[Val]-[Phg]-NH—CH(Me)-pCl-phenyl;
C$_6$H$_5$—O—CO-[Val]-[Phg]-NH—CH(Me)-pCl-phenyl;

C₆H₅—CH₂—O—CO-[Val]-[Phg]-NH—CH(Me)-pCl-phenyl;
Me₂—CH—O—CO-[Val]-[Phg]-NH—CH(Me)—thiazol—2—yl;
Me₂—CH—O—CO-[Val]-[Phg]-NH—CH(Me)—imidazol—2—yl;
Me₂—CH—O—CO-[Leu]-[Phg]-NH—CH(Me)-pCl-phenyl;
Me₂—CH—O—CO—iso[Leu]-[Phg]-NH—CH(Me)-pCl-phenyl;
Me₂—CH—O—CO-[Val]-[Phe]-NH—CH(Me)-pCl-phenyl;
Me₂—CH—O—CO-[Val]-β[Phe]-NH—CH(Me)-pCl-phenyl;
Me₂—CH—O—CO-[Val]-[Phg]-N—CH—CO—N(Me)—methyl;

Me₂—CH—CO-[Val]-[Phg]-O—CH—Me₂;
Me—CH(O—Ac)—CO-[Val]-[Phg]-O—CH—Me₂;
Me—CH(O—Me)—CO-[Val]-[Phg]-O—CH—Me₂;
phenyl—CH(Me)—CO-[Val]-[Phg]-O—CH—Me₂;
cycloPr—CO-[Val]-[Phg]-O—CH—Me₂;
Me₂—CH—O—CO-[Val]-[Val]-[Phg]-NH—CH(Me)-pCl-phenyl;
Me₂—CH—O—CO—[Leu]-[Val]-[Phg]-NH—CH(Me)-pCl-phenyl;
Me₂—CH—O—CO-[Val]-[Phg]-[Tyr]—NH—CH(Me)₂;
Me₂—CH—O—CO-[Val]-[Val]-[Phg]-[Phg]—NH—CH(Me)₂;
Me₂—CH—O—CO-[Val]-[Val]-[Phg]-[Phe]—O—CH(Me)₂;
Me₂—CH—O—CO-[Val]-[Phe]-[Phe]—NH—CH(Me)-pCl-phenyl;
Me₂—CH—O—CO-[Val]-[Phe]-[Phg]—NH—CH(Me)-pCl-phenyl; and so forth.

The compounds of general formula (I) according to the present invention can be obtained by means of several processes.

When K is different from hydrogen, the compounds having general formula (I) can be obtained by means of a process which can be schematically shown as follows (i):

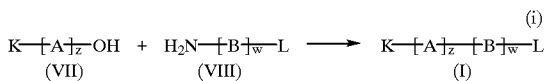

in which K, A, z, B and w have the same meaning as disclosed hereinabove (K different from hydrogen).

The above schematized condensation reaction (i), is carried out by causing the aminoacidic derivatives (VII) to react with a condensation agent such as, e.g., dicyclohexylcarbodiimide or carbonyldiimidazole, in the presence of a polar solvent, e.g., tetrahydrofuran, and subsequently adding the aminoacidic derivatives (VIII). The reaction is carried out at a temperature comprised within the range of from –10° C. to room temperature.

After the addition of the aminoacidic derivative (VIII), the solution is kept with stirring during about 10–15 hours. The resulting compound having general formula (I) is usually purified by crystallization from a suitable solvent such as, e.g., ethylether, isopropylether, methanol, isopropanol, and so forth, or from a mixture of solvents such as, e.g., ethyl ether/methanol, ethyl acetate/hexane, and so forth.

When z is 1, the aminoacidic derivative (VIIa) is obtained by means of a process which can be schematized as follows (ii):

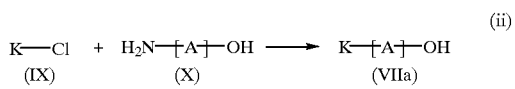

in which K and A have the same meaning as indicated hereinabove (K different from hydrogen).

The condensation reaction (ii) schematized above, between chloride (IX) and the aminoacidic derivative (X) can be carried out both in the presence of protic solvents such as, e.g., water, and in the presence of such organic bases as, e.g., triethylamine or N,N-dimethylaniline as well as in the presence of inorganic bases such as, e.g., sodium hydrogen carbonate, or sodium hydroxide, at a temperature comprised within the range of from –15° C., up to +25° C.

When z is 2, the aminoacidic derivative (VIIb) is obtained by means of a process which can be schematically shown as follows (iii):

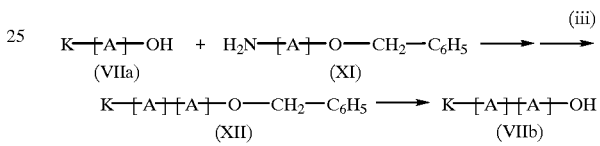

in which K and A have the same meaning as disclosed above (K different from hydrogen).

The condensation reaction (iii) schematically shown above between the aminoacidic derivative (VIIa) and the benzyl ester (XI), is carried out by operating according to the same conditions as disclosed for the reaction reported in above Scheme (i). The benzyl ester of dipeptide (XII) obtained in that way, is converted into the aminoacidic derivative (VIIb) by catalytic hydrogenation, using palladium on charcoal as the catalyst, in the presence of an alcohol solvent, such as, e.g., methanol, ethanol, and so forth, at room temperature.

When w is 1, the aminoacidic derivative (VIIIa) is obtained by means of a process which can be schematically shown as follows (iv):

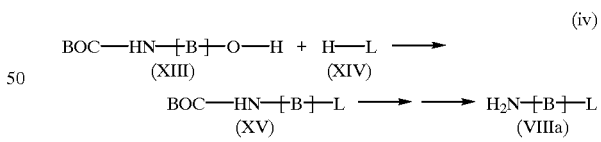

in which B and L have the same meaning as disclosed above.

The reaction (iv) schematically shown above, between the aminoacidic derivative (XIII), protected at its aminic function by means of a benzylcarboxy (BOC) group and compound (XIV), is carried out by operating according to the same conditions as disclosed for the reaction shown Scheme (i). The protective group (BOC) on the resulting compound (XV) is subsequently removed by acidic hydrolysis in ethyl acetate, at room temperature, according to as reported in Bulletin of Chemical Society Japanese (1977), page 718.

When w is 2, the aminoacidic derivative (VIIIb) is carried out by means of a process which can be schematically shown as follows (v):

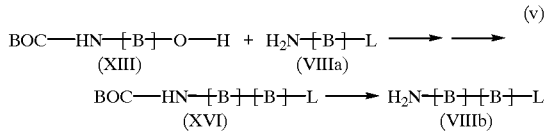

wherein B and L have the same meaning as disclosed above.

The above schematized conjugation reaction (v) between the aminoacidic derivative (XIII) protected at its aminic function by means of a benzylcarboxy (BOC) group and the aminoacidic derivative (VIIIa), is carried out by operating according to the same conditions as disclosed for the reaction displayed in Scheme (i). The protective group (BOC) on the resulting compound (XVI) is then removed by acidic hydrolysis in ethyl acetate, at room temperature according to as reported in Bulletin of Chemical Society Japanese (1977), page 718.

When K stands for hydrogen, the compounds having general formula (I) can be easily obtained by treating a compound having general formula (XVII):

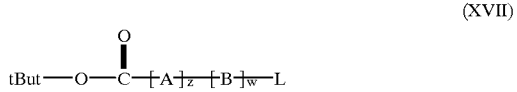

wherein tBut indicates tert-butoxy, A, z, B, w and L have the same meaning as disclosed above, with an acidic solution af aqueous ethyl acetate, at room temperature, according to as reported in Bulletin of Chemical Society Japanese (1977), page 718.

[A] and [B] aminoacids, when they are not commercial products, can be prepared according to what disclosed in published papers, such as, e.g., in Houben-Weyl, "Methoden der Organischen Chemie", Vol. 15: Synthese von Peptiden I and II,(1974); Greenstein-Winitz, "Chemistry of The Aminoacids", (1961) John Wiley Inc.; Synthetic Communications (1993), pages 349–356; Tetrahedron Letters (1975), pages 4393–4394; Tetrahedron Letters (1988), pages 6465–6466.

The compounds having general formula (I) display particularly high fungicidal activity against phytopathogenic fungi which attack vine, sugar beet, cereal, cucurbits and orchard crops.

The plant diseases which can be combatted with the compounds having the general formula (I) according to the present invention are, e.g., the following:

*Plasmopara viticola* on vines;
*Sphaerotheca fuliginea* on cucurbits;
Phythium on horticultural crops;
Phytophthora spp. on horticultural crops;
*Helminthosporium teres* on cereals;
*Erisyphe graminis* on cereals;
Puccinia spp. on cereals;
Septoria sop. on cereals;
Rhynchosporium on cereals;
*Podosphera leucotricha* on cereals;
*Uncinula necator* on vines;
Venturia spp. on fruit trees;
*Pyricularia oryzae* on rice;
*Botrytis cinerea;*
Fusarium spp. on cereals, and so forth.

The compounds having the general formula (I) are capable of displaying a fungicidal action with both curative and preventive character and, additionally, display a low toxicity for plants, or do not display any such toxicity at all.

For practical uses in agriculture, having available fungicidal compositions containing one or more compounds having general formula (I), possibly also as an isomer mixture, as the active substance, is often useful.

The application of these compositions can be carried out on any portions of the plant, e.g., on leaves, stems, branches and roots, or on the same seeds before sowing, or also to the locus on which the plant grows.

Compositions can be used which appear as dry dusts, wettable dusts, emulsified concentrates, microemulsions, pastes, granulates, solutions, suspensions, and so forth: the selection of the type of composition will depend on the specific use.

The compositions are prepared by any modalities known from the prior art, for example, by diluting or dissolving the active substance with a solvent means and/or a solid diluent, possibly in the presence of surfactants.

As solid diluents, or carriers, the following can be used: silica, China clay, bentonite, talc, fossil meal, dolomite, calcium carbonate, magnesia, chalk, clays, synthetic silicate, attapulgite, sepiolite.

As liquid diluents, of course beside water, several solvents can be used, e.g., aromatics (xylenes or mixtures of alkylbenzenes), chloroaromatics (chlorobenzene), paraffins (petroleum fractions), alcohols (methanol, propanol, butanol, octanol, glycerol), amines, amides (N,N-dimethylformamide, N-methylpyrrolidone), ketones (cyclohexanone, acetone, acetophenone, isoforone, ethylamylketone), esters (isobutyl acetate).

As surfactants, there can be used sodium, calcium, triethanolamine or triethylamine salts of alkylsulfonates, alkylarylsulfonates, polyethoxylated alkylphenols, fatty alcohols condensed with ethylene oxide, polyoxyethylated fatty acids, polyoxyethylated sorbitol esters, lignine sulfonates.

The compositions can also contain special additives for particular purposes such as, e.g., adhesion promoters, such as gum arabic, polyvinyl alcohol, polyvinylpyrrolidone.

If so desired, to the compositions according to the present invention also other compatible substances can be added, such as, e.g., fungicides, phytoregulants, antibiotics, herbicides, insecticides, fertilizers.

The concentration of active substance in the above said composition can vary within a wide range, according to the active compound, the crop, the pest, the environmental conditions and the adopted formulation type.

In general, the active substance concentration is comprised within the range of from 0.1% to 95%, preferably of from 0.5% to 90%.

The following examples are reported for illustrative purposes and shall not be construed as being limitative of the present invention.

EXAMPLE 1

Synthesis of N-(tert.-butyloxycarbonyl)-L-valinyl-DL-phenylglycine-4-chlorophenylethylamide (Compound No. 1).

1.3 g of carbonyldiimidazole is added to a solution of 1.5 g of tert.-butyloxycarbonyl-L-valine in 10 cm³ of tetrahydrofuran, with stirring and under a flowing nitrogen stream.

After 20 minutes at the temperature of 25° C., a solution of 2.0 g of DL-phenyl-glycine-4-chlorophenylethylamide in 5 cm³ of tetrahydrofuran is added dropwise during 5 minutes.

After being kept stirred overnight, the reaction mixture is dropped into 100 cm³ of water, and is extracted with ethyl acetate (2×50 cm$^3$). The organic phase is washed with water and is then thoroughly desiccated over sodium sulphate and is evaporated under vacuum.

The resulting raw product is purified by crystallization, using ethyl ether as solvent.

1.3 g of desired compound is obtained, in a yield of 40% ($[\alpha]^D$(CH$_2$Cl$_2$)=−14.20°).

EXAMPLE 2

Synthesis of L-valinyl-DL-phenylglycine-4-chlorophenylethylamide (Compound No. 42)

3 cm$^3$ of aqueous 37% hydrochloric acid is added to solution of 1.0 g of N-(tert.-butyloxycarbonyl)-L-valinyl-DL-phenylglycine-4-chlorophenylethylamide in 10 cm$^3$ of ethyl acetate.

The reaction is kept with stirring for 1 hour at 25° C., the solvent is then vacuum evaporated and the raw residue obtained is taken up with 10 cm$^3$ of ethyl ether and water.

The organic phase is removed, the solution is neutralized with sodium hydrogen carbonate, then is extracted with ethyl acetate (2×10 cm$^3$). The organic phase is desiccated over sodium sulphate, and evaporated.

0.500 g of desired compound is obtained in a yield of 65%. ($[\alpha]^D$(CH$_2$Cl$_2$)=−98.50°).

EXAMPLES 3–54

By operating analogously to Examples 1 and 2, compound nos. 2–41 and nos. 43–54 were prepared, the structures of which are reported in Tables 1–5, together with their elemental analysis results.

EXAMPLE 55

Syntesis of N-(tert.-butyloxycarbonyl)-L-valinyl-DL-β-phenyl-β-alanine ester (Compound No. 55).

An amount of 1.1 g of cyclohexylcarbodiimide was added to a solution, kept cooled at 0° C., obtained by mixing 0.9 g of tert.-butyloxycarbonyl-L-valine, 1.2 g of isopropyl 3-phenyl-3-aminopropanoate hydrochloride (β-phenyl-β-alanine hydrochloride) and 0.46 g of triethylamine in 10 cm$^3$ in metilene chloride.

After 1 hour at room temperature, the obtained solution is evaporated under reduced pressure and the resulting raw product is purified on silica, using a mixture of 3:7 ethyl acetate:hexane as the solvent.

1.5 g of desired compound is obtained in a yield of 85%. ($[\alpha]^D$(CH$_2$Cl$_2$)=−13.80°).

EXAMPLES 56–95

By operating analogously to Example 55, the compound nos. 56–95 were prepared, the structures of which are reported in Tables 6–10, together with their elemental analysis results.

EXAMPLE 96

Determination of Preventive Fungicidal Activity Against Downy Mildew of Vines (*Plasmopara viticola*).

Leaves of vine plants cultivar Dolcetto, grown in pots inside a conditioned room (20±1° C., relative humidity 70%), are spray treated on both their leaf faces with compounds 1–95 in water-acetone solution at 20% acetone by volume.

After a 24-hour stay in conditioned environment, on both leaf faces of the plants, an aqueous suspension of conidia of *Plasmopara viticola* (200,000 conidia per cm$^3$) is sprayed.

The plants are kept in a moisture saturated environment, at 21° C., during the fungus incubation time.

At the end of said time period (7 days), the fungicidal activity is evaluated according to a percent evaluation scale from 100 (healthy plant) to 0 (completely infected plant).

All synthetized compounds displayed a higher control rate than 90, at their use concentration of 500 ppm.

EXAMPLE 97

Determination of Preventive Fungicidal Activity Against Cucumber Powdery Mildew (*Sphaerotheca fuliginea*).

Leaves of cucumber cultivar Marketer, grown in pots inside a conditioned room (20±1° C., relative humidity 70%), are spray treated on both their leaf faces with compounds 1–95 in water-acetone solution at 20% acetone by volume.

After a 24-hour stay in conditioned environment, on both leaf faces of the plants, an aqueous suspension of conidia of *Sphaerotheca fuliginea* (200,000 conidia per cm$^3$) is sprayed.

The plants are kept in a moisture saturated environment, at 2120 C., during the fungus incubation time.

At the end of said time period (8 days), the fungicidal activity is evaluated according to a percent evaluation scale from 100 (healthy plant) to 0 (completely infected plant).

All synthetized compounds displayed a higher control rate than 90, at their use concentration of 1000 ppm.

TABLE 1

Compounds of formula (I) in which: z and w = 1, n = 0, x = —N(R$^3$)—

| COMPOUND No. | K | —[—A—]$_z$— | —[—B—]$_w$— | L |
|---|---|---|---|---|
| 1 | (CH$_3$)$_3$—C—O—CO— | —L[Val]— | —DL[Phg]— | —NH—CH(CH$_3$)—(4Cl)C$_6$H$_4$ |
| 2 | (CH$_3$)$_3$—C—O—CO— | —L[Val]— | —D[Phg]— | —NH—CH(CH$_3$)—(4Cl)C$_6$H$_4$ |
| 3 | (CH$_3$)$_3$—C—O—CO— | —L[Val]— | —DL[Phg]— | —NH—CH(CH$_3$)$_3$ |
| 4 | (CH$_3$)$_3$—C—O—CO— | —L[Val]— | —DL[Phg]— | —NH—CH(CN)—C$_6$H$_5$ |
| 5 | (CH$_3$)$_3$—C—O—CO— | —L[Val]— | —DL[Phg]— | —NH—CH$_2$(4Cl)C$_6$H$_4$ |
| 6 | (CH$_3$)$_3$—C—O—CO— | —L[Val]— | —DL[Phg]— | —NH—CH$_2$(4CH$_2$—O)C$_6$H$_4$ |
| 7 | (CH$_3$)$_3$—C—O—CO— | —L[Val]— | —DL[Phg]— | —NH—CH(CH$_2$)$_2$—CN |
| 8 | (CH$_3$)$_3$—C—O—CO— | —D[Val]— | —DL[Phg]— | (+)-NH—CH(CH$_3$)—(4Cl)C$_6$H$_4$ |
| 9 | (CH$_3$)$_3$—C—O—CO— | —D[Val]— | —DL[Phg]— | (−)-NH—CH(CH$_3$)—(4Cl)C$_6$H$_4$ |

TABLE 1-continued

Compounds of formula (I) in which: z and w = 1, n = 0, x = —N(R³)—

| No. | K | —[—A—]$_s$— | —[B—]$_w$— | L |
|---|---|---|---|---|
| 10 | (CH₃)₃—C—O—CO— | —L[Val]— | —DL[Phg]— | —N(CH₃)—CH₃ |
| 11 | (CH₃)₃—C—O—CO— | —L[Val]— | —DL[Phg]— | —NH—CH(C₆H₅)—C₄H₅ |
| 12 | (CH₃)₃—C—O—CO— | —L[Val]— | —DL[Phg]— | —NH—(CH₃)₇—CH₃ |
| 13 | (CH₃)₃—C—O—CO— | —L[Val]— | —DL[Phg]— | —NH—CH₂—(2,4Cl₂)C₆H₄ |
| 14 | (CH₃)₃—C—O—CO— | —L[Ile]— | —DL[Phg]— | —NH—CH(CH₃)—(4Cl)C₆H₄ |
| 15 | (CH₃)₃—C—O—CO— | —L[Leu]— | —DL[Phg]— | —NH—CH(CH₃)—(4Cl)C₆H₄ |
| 16 | (CH₃)₃—C—O—CO— | —L[Val]— | —DL[Phg]— | —NH—(CH₂)₃—(4Cl)C₆H₄ |
| 17 | (CH₃)₃—C—O—CO— | —L[Val]— | —DL[Phg]— | —N(—(CH₂)₃—)₂—O (morpholino-type) |
| 18 | (CH₃)₃—C—O—CO— | —L[Val]— | —DL[Phg]— | —NH—CH(CH₃)—(4Br)C₆H₄ |
| 19 | C₆H₅—O—CO— | —L[Val]— | —DL[Phg]— | —NH—CH(CH₃)—(4Cl)C₆H₄ |
| 20 | (CH₃)₃—C—O—CO— | —L[Pro]— | —DL[Phg]— | —NH—CH(CH₃)—(4Cl)C₆H₄ |

| COMPOUND No. | ELEMENTAL ANALYSIS | | |
|---|---|---|---|
| | C %, theor. | H %, theor. | N %, theor. |
| 1 | 63.92 (63.99) | 7.10 (7.02) | 8.57 (8.61) |
| 2 | 63.95 (63.99) | 7.00 (7.02) | 8.66 (8.61) |
| 3 | 64.41 (64.43) | 8.45 (8.50) | 10.82 (10.73) |
| 4 | 67.28 (67.22) | 6.95 (6.94) | 12.00 (12.06) |
| 5 | 63.30 (63.35) | 6.83 (6.80) | 8.91 (8.86) |
| 6 | 66.49 (66.50) | 7.50 (7.51) | 9.00 (8.95) |
| 7 | 63.39 (63.44) | 7.70 (7.74) | 13.48 (13.45) |
| 8 | 63.94 (63.99) | 6.99 (7.02) | 8.65 (8.61) |
| 9 | 64.02 (63.99) | 7.00 (7.02) | 8.64 (8.61) |
| 10 | 63.62 (63.64) | 8.25 (8.28) | 11.18 (11.13) |
| 11 | 72.26 (72.21) | 7.19 (7.23) | 8.09 (8.15) |
| 12 | 67.67 (67.65) | 9.30 (9.39) | 9.18 (9.10) |
| 13 | 59.11 (59.06) | 6.17 (6.15) | 8.23 (8.26) |
| 14 | 64.52 (64.59) | 7.20 (7.23) | 8.41 (8.37) |
| 15 | 64.54 (64.59) | 7.20 (7.23) | 8.39 (8.37) |
| 16 | 63.95 (63.99) | 6.95 (7.02) | 8.58 (8.61) |
| 17 | 63.07 (62.99) | 8.02 (7.93) | 10.12 (10.02) |
| 18 | 58.60 (58.65) | 6.38 (6.44) | 7.88 (7.89) |
| 19 | 66.30 (66.20) | 6.01 (5.95) | 8.35 (8.27) |
| 20 | 64.21 (64.26) | 6.62 (6.64) | 8.61 (8.65) |

TABLE 2

Compounds of formula (I) in which: z and w = 1, n = 0, x = —O—

| COMPOUND No. | K | —[—A—]$_s$— | —[B—]$_w$— | L | ELEMENTAL ANALYSIS | | |
|---|---|---|---|---|---|---|---|
| | | | | | C %, theor. | H %, theor. | N %, theor. |
| 21 | (CH₃)₃—C—O—CO— | —L[Val]— | —D[Phg]— | —O—CH₃ | 62.60 (62.62) | 7.69 (7.74) | 7.72 (7.69) |
| 22 | (CH₃)₃—C—O—CO— | —L[Val]— | —L[Phg]— | —O—CH₃ | 62.50 (62.62) | 7.71 (7.74) | 7.63 (7.69) |
| 23 | (CH₃)₃—C—O—CO— | —L[Val]— | —DL[Phg] | —O—CH(CH₃)₃ | 64.34 (64.26) | 8.31 (8.22) | 7.04 (7.14) |
| 24 | (CH₃)₃—C—O—CO— | —L[Val]— | —D[Phg]— | —O—CH(CH₃)₃ | 64.22 (64.26) | 8.17 (8.22) | 7.13 (7.14) |
| 25 | (CH₃)₃—C—O—CO— | —L[Val]— | —DL[Phg]— | —O—CH(CH₃)₃ | 64.22 (64.26) | 8.23 (8.22) | 7.15 (7.14) |
| 26 | (CH₃)₃—C—O—CO— | —L[Val]— | —DL[Phg](4Cl)— | —O—CH(CH₃)₃ | 59.16 (59.08) | 7.39 (7.32) | 6.50 (6.56) |
| 27 | (CH₃)₃—C—O—CO— | —L[Val]— | —D[Phg]— | —O—CH(CH₃)₃ | 64.28 (64.26) | 8.28 (8.22) | 7.09 (7.14) |
| 28 | C₆H₅—CH₃—O—CO— | —L[Pro]— | —DL[Phg]— | —O—CH(CH₃)₃ | 67.87 (67.91) | 6.59 (6.65) | 6.69 (6.60) |

TABLE 3

Compounds of formula (I) in which: z and w = 1, n = 1

| COMPOUND No. | K | —[—A—]$_s$— | —[B—]$_w$— | L | ELEMENTAL ANALYSIS | | |
|---|---|---|---|---|---|---|---|
| | | | | | C %, theor. | H %, theor. | N %, theor. |
| 29 | (CH₃)₃—C—O—CO— | —L[Val]— | —DL[Phe]— | —NH—CH(CH₃)—(4Cl)C₆H₅ | 64.40 (64.59) | 7.19 (7.23) | 8.40 (8.37) |

TABLE 3-continued

Compounds of formula (I) in which: z and w = 1, n = 1

| COMPOUND No. | K | —[—A—]$_a$— | —[B—]$_w$— | L | ELEMENTAL ANALYSIS C %, theor. | H %, theor. | N %, theor. |
|---|---|---|---|---|---|---|---|
| 30 | (CH$_3$)$_3$—C—O—CO— | —D[Val]— | —DL[Phe]— | —O—CH(CH$_3$)$_2$ | 64.98 (65.00) | 8.37 (8.43) | 6.94 (6.89) |
| 31 | (CH$_3$)$_3$—C—O—CO— | —L[Val]— | —DL[Phe]— | —O—CH(CH$_3$)$_2$ | 64.93 (65.00) | 8.39 (8.43) | 6.88 (6.89) |
| 32 | (CH$_3$)$_3$—C—O—CO— | —L[Val]— | —DL[Tyr]— | —O—CH(CH$_3$)$_2$ | 62.13 (62.54) | 8.18 (8.11) | 6.32 (6.23) |
| 33 | (CH$_3$)$_3$—C—O—CO— | —L[Val]— | —DL[Tyr](CH$_3$)— | —O—CH(CH$_3$)$_2$ | 63.32 (63.28) | 8.39 (8.31) | 6.38 (6.42) |
| 34 | (CH$_3$)$_3$—C—O—CO— | —L[Val]— | —DL[Tyr](CH$_3$)— | —NH—CH(CH$_3$)— (4Cl)C$_6$H$_5$ | 63.22 (63.21) | 7.14 (7.20) | 7.97 (7.90) |

TABLE 4

Compounds having formula (I) in which: z and w = 1, n = 0, further examples for K

| COMPOUND No. | K | —[—A—]$_a$— | —[B—]$_w$— | L | ELEMENTAL ANALYSIS C %, theor. | H %, theor. | N %, theor. |
|---|---|---|---|---|---|---|---|
| 35 | C$_3$H$_6$—O—(CO)$_3$— | —L[Val]— | —DL[Phg]— | —NH—CH(CH$_3$)— (4Cl)C$_6$H$_5$ | 61.49 (61.53) | 6.13 (6.20) | 8.65 (8.61) |
| 36 | CH$_3$—O—CO—CH$_3$—CO— | —L[Val]— | —DL[Phg]— | —NH—CH(CH$_3$)— (4Cl)C$_6$H$_5$ | 61.56 (61.53) | 6.25 (6.20) | 8.62 (8.61) |
| 37 | cicloC$_3$H$_6$—CO— | —L[Val]— | —DL[Phg]— | —NH—CH(CH$_3$)— (4Cl)C$_6$H$_5$ | 65.87 (65.85) | 6.66 (6.63) | 9.17 (9.22) |
| 38 | cicloC$_3$H$_6$—CO— | —L[Val]— | —D[Phg]— | —O—CH(CH$_3$)$_3$ | 66.62 (66.64) | 7.79 (7.83) | 7.70 (7.77) |
| 39 | C$_6$H$_5$—CH(CH$_3$)—CO— | —L[Val]— | —D[Phg]— | —O—CH(CH$_3$)$_2$ | 70.81 (70.73) | 7.68 (7.60) | 6.54 (6.60) |
| 40 | H— | —L[Val]— | —D[Phg]— | —O—CH(CH$_3$)$_2$ | 65.70 (65.73) | 8.21 (8.27) | 9.64 (9.58) |
| 41 | H— | —L[Val]— | —DL[Phg](4Cl)— | —O—CH(CH$_3$)$_2$ | 58.93 (58.80) | 7.01 (7.09) | 8.52 (8.57) |
| 42 | H— | —L[Val]— | —DL[Phg]— | —O—CH(CH$_3$)$_2$ | 65.65 (65.73) | 8.25 (8.27) | 9.63 (9.58) |
| 43 | H— | —L[Val]— | —DL[Phg]— | —NH—CH(C$_6$H$_5$)—C$_6$H$_5$ | 75.07 (75.15) | 7.10 (7.03) | 10.06 (10.11) |
| 44 | H— | —L[Val]— | —DL[Phg]— | —NH—CH(CH$_3$)— (4Cl)C$_6$H$_5$ | 65.09 (65.02) | 8.45 (8.43) | 10.79 (10.83) |

TABLE 5

Compounds of formula (I) in which: z or w = 2

| COMPOUND No. | K | —[—A—]$_a$— | —[B—]$_w$— | L | ELEMENTAL ANALYSIS C %, theor. | H %, theor. | N %, theor. |
|---|---|---|---|---|---|---|---|
| 45 | (CH$_3$)$_3$—C—O—CO— | —L[Val]—L[Val]— | —DL[Phg]— | —O—CH(CH$_3$)$_2$ | 63.20 (63.52) | 8.45 (8.41) | 8.42 (8.55) |
| 46 | H— | —L[Val]—L[Val]— | —DL[Phg]— | —O—CH(CH$_3$)$_2$ | 64.38 (64.43) | 8.53 (8.50) | 10.85 (10.73) |
| 47 | (CH$_3$)$_3$—C—O—CO— | —L[Leu]—L[Val]— | —DL[Phg]— | —O—CH(CH$_3$)$_2$ | 64.33 (64.13) | 8.59 (8.57) | 8.35 (8.31) |
| 48 | (CH$_3$)$_3$—C—O—CO— | —L[Val]— | —DL[Phg]—DL[Phg]— | —O—CH(CH$_3$)$_2$ | 66.19 (66.27) | 7.43 (7.48) | 8.02 (7.99) |
| 49 | (CH$_3$)$_3$—C—O—CO— | —L[Val]— | —DL[Phg]—DL[Phg]— | —NH—CH(CH$_3$)— (4Cl)C$_6$H$_5$ | 65.78 (65.74) | 6.61 (6.65) | 9.10 (9.02) |
| 50 | (CH$_3$)$_3$—C—O—CO— | —L[Val]— | —DL[Phg]—DL[Phe]— | —O—CH(CH$_3$)$_2$ | 66.75 (66.77) | 7.63 (7.66) | 7.82 (7.79) |
| 51 | (CH$_3$)$_3$—C—O—CO— | —L[Val]— | —DL[Phg]— | —O—CH(CH$_3$)— (4Cl)C$_6$H$_5$ | 63.83 (63.86) | 6.76 (6.80) | 5.75 (5.73) |
| 52 | (CH$_3$)$_3$—C—O—CO— | —L[Val]— | —DL[Phg]— | —NH—O—CH$_3$— (4iPro)C$_6$H$_5$ | 65.51 (65.48) | 7.67 (7.65) | 8.12 (8.18) |
| 53 | (CH$_3$)$_3$—C—O—CO— | —L(CH$_2$)[Val]— | —DL[Phg]— | —NH—CH(CH$_3$)— (4Cl)C$_6$H$_5$ | 64.61 (64.59) | 7.20 (7.23) | 8.40 (8.37) |
| 54 | (CH$_3$)$_3$—C—O—CO— | —L[Val]— | —DL[Phg]— | —O—CH(CH$_3$)— CO-(piperidyl) | 63.79 (63.78) | 8.10 (8.03) | 8.59 (8.58) |

TABLE 6

Compounds of formula (I) in which z and w = 1, n = 0, m = 1, x = 0

| Compound No. | K | [—A—]$_z$— | [—B—]$_w$— | L | % C (theor.) | % H (theor.) | % N (theor.) |
|---|---|---|---|---|---|---|---|
| 55 | (CH$_3$)$_3$—C—O—CO— | —L[Val]— | —DL—B[Phe]— | —O—CH(CH$_3$)$_3$ | 64.98 (65.00) | 8.47 (8.43) | 6.84 (6.89) |
| 56 | " | " | —D—B[Phe]— | " | 65.01 (65.00) | 8.46 (8.43) | 6.87 (6.89) |
| 57 | " | " | —L—B[Phe]— | " | 65.01 (65.00) | 8.42 (8.43) | 6.85 (6.89) |
| 58 | (CH$_3$)$_2$—CH—O—CO— | " | —DL—B[Phe] | " | 64.29 (64.26) | 8.18 (8.22) | 7.17 (7.14) |
| 59 | H$_2$C=CH—CH$_2$—O—CO— | " | " | " | 64.63 (64.60) | 7.77 (7.74) | 7.17 (7.17) |
| 60 | C$_2$H$_5$—O—CO— | " | " | " | 67.62 (67.59) | 7.00 (7.09) | 6.60 (6.57) |
| 61 | Cl$_3$C—CH$_2$—O—CO— | " | " | " | 49.83 (49.86) | 5.68 (5.65) | 5.76 (5.81) |
| 62 | Cl$_3$C—C(Me)$_2$—O—CO— | " | " | " | 51.85 (51.83) | 6.15 (6.13) | 5.47 (5.49) |
| 63 | iPr—O—CO—CH(Me)—O—CO— | " | " | " | 62.01 (62.05) | 7.80 (7.81) | 6.06 (6.03) |
| 64 | (CH$_3$)$_3$—C—O—CO— | " | —DL—B[Tyr](Me)— | " | 63.31 (63.28) | 8.29 (8.31) | 6.45 (6.42) |

TABLE 7

Compounds of formula (I) in which z and w = 1, n = 0, m = 1

| Compound No. | K | [—A—]$_z$— | [—B—]$_w$— | L | % C (theor.) | % H (theor.) | % N (theor.) |
|---|---|---|---|---|---|---|---|
| 65 | (CH$_3$)$_3$—C—O—CO— | —L[Val]— | —DL—B[Phe](4Cl)— | —O—CH(CH$_3$)$_2$ | 59.88 (59.92) | 7.57 (7.54) | 6.33 (6.35) |
| 66 | (CH$_3$)$_3$—C—O—CO— | " | —DL—B[Phe](3,4Cl$_2$)— | " | 55.60 (55.58) | 6.78 (6.78) | 5.88 (5.89) |
| 67 | (CH$_3$)$_3$—C—O—CO— | " | —DL—B[Tyr](Me)(3OMe) | " | 61.79 (61.78) | 8.25 (8.21) | 6.07 (6.00) |
| 68 | (CH$_3$)$_3$—C—O—CO— | " | —DL—B—[Phe]— | —O—CH$_2$—cC$_3$H$_5$ | 66.01 (66.01) | 8.17 (8.19) | 6.72 (6.69) |
| 69 | (CH$_3$)$_3$—C—O—CO— | " | " | —O—CH$_2$—C$_6$H$_5$ | 68.11 (68.16) | 7.40 (7.32) | 6.38 (6.36) |
| 70 | (CH$_3$)$_3$—C—O—CO— | " | " | —O—C—(CH$_3$)$_3$ | 65.73 (65.69) | 8.60 (8.63) | 6.68 (6.66) |
| 71 | (CH$_3$)$_3$—C—O—CO— | " | " | —O—CH$_2$—C—(CH$_3$)$_3$ | 66.30 (66.33) | 8.79 (8.81) | 6.47 (6.45) |
| 72 | (CH$_3$)$_3$—C—O—CO— | " | " | —NH—CH—(CH$_3$)$_2$ | 65.11 (65.16) | 8.75 (8.70) | 10.32 (10.36) |
| 73 | (CH$_3$)$_3$—C—O—CO— | " | " | —N(Me)—CH$_2$—COO—iPr. | 62.89 (62.87) | 8.26 (8.23) | 8.75 (8.80) |
| 74 | (CH$_3$)$_3$—C—O—CO— | " | " | —N(Me)—CH$_2$—COO—C$_2$H$_5$ | 62.13 (62.18) | 8.09 (8.04) | 9.01 (9.06) |

TABLE 8

Compounds of formula (I) in which z and w = 1, n = 0, m = 1

| Compound No. | K | [—A—]$_z$— | [—B—]$_w$— | L | % C (theor.) | % H (theor.) | % N (theor.) |
|---|---|---|---|---|---|---|---|
| 75 | (CH$_3$)$_3$—C— | —L—(Me)[Val]— | —DL—B[Phe]— | —O—CH(CH$_3$)$_2$ | 65.60 (65.69) | 8.58 (8.63) | 6.70 (6.66) |
| 76 | " | " | —DL—B(Me)[Phe]— | O—CH(CH$_3$)$_2$ | 66.29 (66.33) | 8.86 (8.81) | 6.50 (6.45) |
| 77 | " | —L—[Val]— | —DL—B(Me)[Phe]— | " | 65.59 (65.69) | 8.65 (8.63) | 6.64 (6.66) |

TABLE 9

Compounds of formula (I) in which z and w = 1, n = 0, m = 1, x = 0

| Compound No. | K | [—A—]$_z$— | [—B—]$_w$— |
|---|---|---|---|
| 78 | (CH$_3$)$_3$—C—O—CO— | —L—[Val]— | —DL—β[Phe]— |
| 79 | CF$_3$—CO— | —L—[Val]— | —DL—β[Phe]— |
| 80 | CH$_3$—CO— | —L—[Val]— | —DL—β[Phe]— |
| 81 | cC$_4$H$_7$—CO— | —L—[Val]— | —DL—β[Phe]— |
| 82 | 4-MeO(C$_6$H$_5$)—CO— | —L—[Val]— | —DL—β[Phe]— |
| 83 | 4-Cl(C$_6$H$_5$)—CO— | —L—[Val]— | —DL—β[Phe]— |
| 84 | 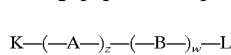 | —L—[Val]— | —DL—β[Phe]— |
| 85 | 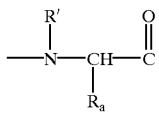 | —L—[Val]— | —DL—β[Phe]— |
| 86 | Thza*—CO— | —L—[Val]— | —DL—β[Phe]— |
| 87 | Thzb**—CO— | —L—[Val]— | —DL—β[Phe]— |

| Compound No. | L | Elemental Analysis % C (theor.) | % H (theor.) | % N (theor.) |
|---|---|---|---|---|
| 78 | —[Pro]—OiPr | 64.42 (64.39) | 8.21 (8.21) | 8.38 (8.34) |
| 79 | —O—CH—(CH$_3$)$_2$ | 56.77 (56.71) | 6.22 (6.26) | 14.10 (14.16) |
| 80 | —O—CH—(CH$_3$)$_2$ | 65.45 (65.49) | 8.08 (8.10) | 8.07 (8.04) |
| 81 | —O—CH—(CH$_3$)$_2$ | 67.96 (68.01) | 8.36 (8.30) | 7.29 (7.21) |
| 82 | —O—CH—(CH$_3$)$_2$ | 68.19 (68.16) | 7.29 (7.32) | 6.40 (6.36) |
| 83 | —O—CH—(CH$_3$)$_2$ | 64.81 (64.78) | 6.53 (6.57) | 6.30 (6.30) |
| 84 | —O—CH—(CH$_3$)$_2$ | 68.20 (68.16) | 7.35 (7.32) | 6.38 (6.36) |
| 85 | —O—CH—(CH$_3$)$_2$ | 63.25 (63.22) | 6.60 (6.58) | 5.90 (5.90) |
| 86 | —O—CH—(CH$_3$)$_2$ | 61.21 (61.23) | 6.78 (6.77) | 9.75 (9.74) |
| 87 | —O—CH—(CH$_3$)$_2$ | 62.10 (62.00) | 7.06 (7.01) | 9.40 (9.43) |

*Thza = 2-methyl-thiazol-4-yl
**Thzb = 2,5-dimethyl-thiazol-4-yl

TABLE 10

Compounds of formula (I) in which w = 1, n = 0, m = 1, x = 0

| Compound No. | K | [—A—]$_z$— | —B—]$_w$— | L | Elemental Analysis % C (theor.) | % H (theor.) | % N (theor.) |
|---|---|---|---|---|---|---|---|
| 88 | (CH$_3$)$_3$—C— | —L—[Val]— | 3,4-methylenedioxyphenyl | —O—CH(CH$_3$)$_2$ | 61.33 (61.32) | 7.65 (7.61) | 6.24 (6.22) |
| 89 | " | " | 4,5-dimethylthiazol-2-yl | " | 57.10 (57.12) | 7.80 (7.99) | 9.55 (9.52) |
| 90 | " | " | napht-1-yl | " | 68.42 (68.40) | 7.95 (7.95) | 6.12 (6.14) |
| 91 | " | " | napht-2-yl | " | 68.45 (68.40) | 7.98 (7-98) | 6.15 (6.14) |
| 92 | " | " | benzothiazol-2-yl | " | 59.61 (59.59) | 7.16 (7.17) | 9.08 (9.06) |
| 93 | " | " | benzooxazol-2-yl | " | 61.70 (61.73) | 7.44 (7.43) | 9.40 (9.39) |
| 94 | " | " | benzofuran-2-yl | " | 64.56 (64.55) | 7.69 (7.67) | 6.25 (6.27) |
| 95 | " | " | benzothiophen-2-yl | " | 62.33 (62.31) | 7.43 (7.41) | 6.08 (6.08) |

We claim:
1. An oligopeptide compound having the formula (I):

K—(—A—)$_z$—(—B—)$_w$—L         (I)

wherein:

z and w are the same or different from each other and are 1 or 2;

A represents an aminoacidic radical having the formula (II):

$$\begin{array}{c} R' \quad O \\ | \quad \| \\ -N-CH-C- \\ | \\ R_a \end{array}$$         (II)

wherein:

$R_a$ represents a linear or branched $C_3$–$C_4$ alkyl radical or a $C_3$–$C_4$ cycloalkyl radical;

R' represents a hydrogen atom or a $C_1$–$C_3$ alkyl radical;

B represents an aminoacidic radical having the formula (III):

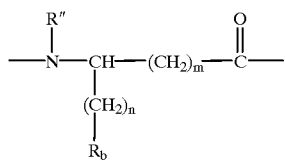

(III)

wherein:

$R_b$ represents an unsubstituted phenyl radical, an unsubstituted naphthyl radical or a substituted phenyl radical or a substituted naphthyl radical which is substituted with one or more halogen atoms, which are the same or different from each other, and are selected from the group consisting of fluorine, chlorine, bromine and iodine, or with one or more groups, which are the same or different from each other, and are selected from the group consisting of linear or branched $C_1$–$C_5$ alkyl or haloalkyl radicals, linear or branched $C_1$–$C_5$ alkoxy, haloalkoxy radicals, $C_3$–$C_6$ cycloalkyl or cycloalkoxy radicals, $C_2$–$C_5$ carbalkoxy radicals, cyano radicals and methylene dioxyl radicals having the formula (VI):

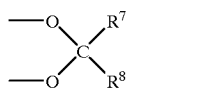

(VI)

wherein:

$R^7$ and $R^8$, which are the same or different from each other, and represent a hydrogen atom, a fluorine atom, a $C_1$–$C_3$ alkyl or haloalkyl radicals;

m is 1 and n is 0 or 1;

R" represents a hydrogen atom or a $C_1$–$C_3$ alkyl radical;

L represents a moiety having the formula (IV):

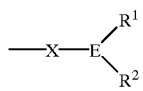

(IV)

wherein:

E represents a linear or branched $C_1$–$C_8$ alkylene or haloalkylene chain, an omega-oxa-$C_2$–$C_8$ alkyl chain or a direct linkage;

$R^1$ represents a hydrogen atom, a $C_3$–$C_6$ cycloalkyl radical or an unsubstituted or substituted phenyl radical;

$R^2$ represents a hydrogen atom, a linear or branched $C_2$–$C_6$ carbamoyl radical, a cyano radical or a halogen atom selected from the group consisting of fluorine, chlorine and bromine;

X represents an —O-moiety; a —N($R^3$)— moiety or a —N($R^4$)—O-moiety, wherein:

$R^3$ represents a hydrogen atom, a $C_1$–$C_3$ alkyl or alkoxy radical, or $R^3$ together with $R^1$, represents a direct linkage or a $C_2$–$C_4$ alkylene chain;

$R^4$ represents a hydrogen atom, a $C_1$–$C_3$ alkyl radical, or $R^4$ together with $R^1$, represents a direct linkage or a $C_2$–$C_4$ alkylene chain;

with the proviso that when X represents an —O— moiety, and E represents a direct linkage, only one of $R^1$ and $R^2$ is present;

K represents a linear or branched $C_1$–$C_4$ alkyl radical or a protective group having the formula (V):

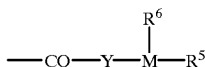

(V)

wherein:

Y represents an oxygen atom or a direct linkage;

M represents a linear, branched or cyclic $C_1$–$C_8$ alkylene or a haloalkylene chain or a direct linkage;

$R^5$ represents a hydrogen atom, a substituted or unsubstituted phenyl radical or an unsubstituted or substituted phenoxy radical;

$R^6$ represents a hydrogen atom, a $C_1$–$C_3$ alkoxy or haloalkoxy radical, an acetate radical, an acetamidic radical or a halogen atom selected from the group consisting of fluorine, chlorine and bromine, with the proviso that when Y represents an oxygen atom, and M represents a direct linkage, only one of $R^5$ and $R^6$ is present.

2. An anti-fungal composition for agricultural purposes, comprising an effective fungicidal amount of at least one oligopeptidic compound having the formula (I):

(I)

wherein:

z and w are the same or different from each other and are 1 or 2; and

A represents an aminoacidic radical having the formula (II):

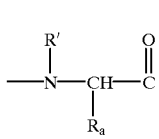

(II)

wherein:

$R_a$ represents a linear or branched $C_3$–$C_4$ alkyl radical or a $C_3$–$C_4$ cycloalkyl radical;

R' represents a hydrogen atom or a $C_1$–$C_3$ alkyl radical;

B represents an aminoacidic radical having the formula (III):

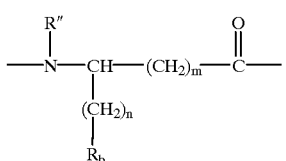

(III)

wherein:

$R_b$ represents an unsubstituted phenyl radical, an unsubstituted naphthyl radical, or a substituted phenyl radical or a substituted naphthyl radical which is substituted with one or more halogen atoms, which are the same or different from each other, and are selected from the group consisting of fluorine, chlorine, bromine and iodine, or with one or more groups, which are the same or different from each other, and are selected from the group consisting of linear or branched $C_1$–$C_5$ alkyl or haloalkyl radicals, linear or branched $C_1$–$C_5$ alkoxy or haloalkoxy radicals, $C_3$–$C_6$ cycloalkyl or cycloalkoxy radicals, $C_2$–$C_5$ carbaalkoxy radicals, cyano radicals and methylene dioxyl radicals having the formula (VI):

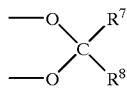

(VI)

wherein:

$R^7$ and $R^8$, which are the same or different from each other, represent a hydrogen atom, a fluorine atom, a $C_1$–$C_3$ alkyl or haloalkyl radicals;

m is 1 and n is 0 or 1;

R" represents a hydrogen atom or a $C_1$–$C_3$ alkyl radical;

L represents a moiety having the formula (IV):

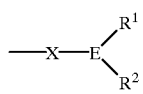

(IV)

wherein:

E represents a linear or branched $C_1$–$C_8$ alkylene or haloalkylene chain, an omega-oxa-$C_2$–$C_8$ alkyl chain or a direct linkage;

$R^1$ represents a hydrogen atom, a $C_3$–$C_6$ cycloalkyl radical, or an unsubstituted or substituted phenyl radical;

$R^2$ represents a hydrogen atom, a linear or branched $C_2$–$C_6$ carboxyalkyl radical, a linear, branched or cyclic $C_2$–$C_6$ carbamoyl radical, a cyano radical or a halogen atom selected from the group consisting of fluorine, chlorine and bromine;

X represents an —O—moiety; a —N($R^3$)-moiety or —N($R^4$)—O moiety, wherein:

$R^3$ represents a hydrogen atom, a $C_1$–$C_3$ alkyl or alkoxy radical, or $R^3$ together with $R^1$, represents a direct linkage or a $C_2$–$C_4$ alkylene chain;

$R^4$ represents a hydrogen atom, a $C_1$–$C_3$ alkyl radical, or $R^4$ together with $R^1$, represents a direct linkage or a $C_2$–$C_4$ alkylene chain;

with the proviso that when X represents an —O— moiety, and E represents a direct linkage, only one of $R^1$ and $R^2$ is present;

K represents a linear or branched $C_1$–$C_4$ alkyl radical or a protective group having the formula (V):

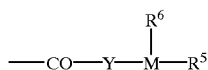

(V)

wherein:

Y represents an oxygen atom or a direct linkage;

M represents a linear, branched or cyclic $C_1$–$C_8$ alkylene or haloalkylene chain or a direct linkage;

$R^5$ represents a hydrogen atom, an unsubstituted phenyl radical or a substituted phenoxy radical;

$R^6$ represents a hydrogen atom, a $C_1$–$C_3$ alkoxy or haloalkoxy radical, an acetate radical, an acetamidic radical or a halogen atom selected from the group consisting of fluorine, chlorine and bromine, with the proviso that when Y represents an oxygen atom, and M represents a direct linkage, only one of $R^5$ and $R^6$ is present; in combination with a solid carrier, a liquid diluent or a surfactant.

3. The antifungal composition for agricultural purposes according to claim 1, in which $R_a$ is selected from the group consisting of: isopropyl, isobutyl, sec.-butyl and tert.-butyl.

4. The antifungal composition for agricultural purposes according to claim 2, in which $R_a$ is selected from the group consisting of: cyclopropyl, methylcyclopropyl and dimethylcyclopropyl.

5. The antifungal composition for agricultural purposes according to claim 2, in which the aminoacidic radical A, when $R_a$ represents a cycloalkyl radical, are selected from the group consisting of: cycloprolylglycine and cyclobutylglycine.

6. The antifungal composition for agricultural purposes according to claim 2, wherein said aminoacidic residue B is selected from the group consisting of (1-methylpyrrol-2-yl) glycine, imidazol-2-yl-glycine, thiazol-2-yl-glycine, (4-phenyl-3-methylthiazol-2-yl)-glycine,(5-trifluoromethylpyrid-2-yl)-glycine and pyrimidin-2-yl-glycine, and n is 0.

7. The antifungal composition for agricultural purposes according to claim 2, wherein said aminoacidic residue B is selected from the group consisting of 3-(1-methylpyrrol-2-yl)alanine, 3-(imidazol-2-yl)alanine, 3-(thiazol-2-yl) alanine, 3-(5-trifluoromethylpyrid-2-yl)alanine, 3-pyrimidin-2-yl-alanine and 3-(3-methoxy-4methyl) isooxazol-5-yl)alanine, and n is 1.

8. The antifungal composition for agricultural purposes according to claim 2, in which L, when X represents an oxygen atom, is selected from the group consisting of: methoxy, ethoxy, isopropoxy, tert.-butoxy and benzyloxy.

9. The antifungal composition for agricultural purposes according to claim 2, in which L, when X represents a —N($R^3$)— moiety, is selected from the group consisting of: methylamino, isopropylamino, butylamino, octylamino, N,N-dimethylamino, piperidyl, morphol-4-yl, benzylamino, 4-chlorobenzylamino, 2,4-dichlorobenzylamino, α-methyl-4-chlorobenzylamino, α-methyl-4-bromobenzylamino, α-methyl-4-methoxybenzylamino, α-methyl-4-trifluoromethylbenzylamino, thiazol-2-ylamino, imidaz-2-ylamino, α-cyanobenzylamino, α-cyanoisopropylamino, α-carbomethoxyethylamino, α-carboispropoxyethylamino, α-carbomethoxyisobutylamino, 2-carboisopropoxypyrrolid-1-yl, α-(N-methylcarbamoyl)ethylamino, α-carbamoylethylamino, 2-(N,N-dimethylcarbamoyl-pyrrolid-1-yl) and 2-(N,N-dimethylcarbamoylpiperid-1-yl).

10. The antifungal composition for agricultural purposes according to claim 2, in which L, when X represents an —N($R^4$)—O— moiety, is selected from the group consisting of: methoxyamino, benzyloxyamino and N-methyl-N-benzyloxyamino.

11. The antifungal composition for agricultural purposes according to claim 2, in which K, when Y represents an oxygen atom, is selected from the group consisting of: carbomethoxy, carboispropoxy, carboisobutoxy, carbo-tert.-butoxy, carbobenzyloxy and carbophenoxy.

12. The antifungal composition for agricultural purposes according to claim 2, in which K, when Y represents a direct bond, is selected from the group consisting of: acetyl, isobutanoyl, benzoyl, cyclopropanoyl, 2-methoxypropanoyl, 2-acetamidopropanoyl and 2-carbomethoxyacetyl.

13. A method for combatting fungal pests comprising applying to one or more of plants, leaves, stems, branches and roots or to seeds before sowing, or to the soil on which the plant grows, the anti-fungal composition according to claim 2.

14. The antifungal composition for agricultural purposes according to claim 2, wherein when $R_a$ represents an alkyl radical, the aminoacidic radical A is selected from the group consisting of L-valine, DL-valine, D-valine, leucine, isoleucine, allo-isoleucine and tert.-leucine.

15. The antifungal composition for agricultural purposes according to claim 2, wherein said aminoacidic radical is selected from the group consisting of proline, 3-methylproline and 3,3-dimethylproline.

16. The antifungal composition for agricultural purposes according to claim 2, wherein when $R_b$ represents an unsubstituted or substituted phenyl radical and n is 0, the aminoacidic radical B is selected from the group consisting of D-phenylglycine, DL-phenylglycine and DL-p-Cl-phenylglycine.

17. The antifungal composition for agricultural purposes according to claim 2, wherein when $R_b$ represents an unsubstituted or substituted phenyl radical and n is equal to 1, the aminoacidic radical B is selected from the group consisting of D-phenylalanine, DL-phenylalanine, D-tyrosine, DL-tyrosine, DL-tyrosine-methylether, DL-3-methoxy-tyrosine-methylether, DL-β-phenylalanine, and β-tyrosine-O-methylether.

18. A process for preparing the oligopeptidic compound according to claim 1, which comprises carrying out a condensation reaction of an aminoacidic compound (VII) and an aminoacidic derivative (VIII) as follows:

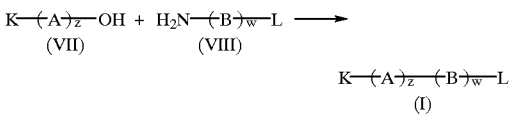

wherein K, A, z, B and w are defined in claim 1, in the presence of a condensing agent and a polar solvent, at a temperature of −10° C. to room temperature.

19. The oligopeptide compound according to claim 1, wherein when $R_a$ is selected from the group consisting of isopropyl, isobutyl, sec.-butyl and tert.-butyl, then A is selected from the group consisting of L-valine, DL-valine, D-valine, leucine, isoleucine, allo-isoleucine and tert-leucine; and when $R_a$ is selected from the group consisting of cyclopropyl, methylcyclopropyl and dimethylcyclopropyl, then A is selected from the group consisting of cycloprolylglycine and cyclobutylglycine.

20. The oligopeptide compound according to claim 1, wherein the aminoacidic residue β is selected from the group consisting of D-phenylglycine, DL-phenylglycine, DL-p-Cl-phenylglycine, D-phenylalanine, DL-phenylalanine, D-tyrosine, DL-tyrosine, DL-tyrosine-methylether, DL-3-methoxy-tyrosine methylether, DL-β-phenylalanine, β-tyrosine-O-methylether, (1-methylpyrrol-2-yl)glycine, imidazol-2-yl-glycine, thiazol-2-yl-glycine, (4-phenyl-3-methylthiazol-2-yl)-glycine, (5-trifluoromethylpyrid-2-yl) glycine, 3-(1-methylpyrrol-2-yl) alanine, 3-(imidazol-2-yl) alanine, 3-(thiazol-2-yl) alanine, 3-(5-trifluoromethylpyrid-2-yl) alanine, 3-pyrimidin-2-yl-alanine and 3-((3-methoxy-4-methyl) isooxazol-5-yl) alanine.

* * * * *